United States Patent [19]

Strong

[11] 4,030,908

[45] June 21, 1977

[54] N-[3-(4-METHYL-3-CYCLOHEXENYL)-BUTYL]AMINES AND THEIR USE AS PLANT GROWTH REGULATORS

[75] Inventor: Jerry G. Strong, Fanwood, N.J.

[73] Assignee: Mobil Oil Corporation, New York, N.Y.

[22] Filed: Feb. 27, 1975

[21] Appl. No.: 553,771

Related U.S. Application Data

[62] Division of Ser. No. 221,384, Jan. 27, 1972, Pat. No. 3,890,384.

[52] U.S. Cl. .................................................. 71/78
[51] Int. Cl.² .......................................... A01N 5/00
[58] Field of Search .............................. 71/78, 121

[56] References Cited

UNITED STATES PATENTS

| | | |
|---|---|---|
| 3,223,517 | 12/1965 | Abramitis et al. ..................... 71/78 |
| 3,471,612 | 10/1969 | Goonewardene ...................... 71/78 |
| 3,672,866 | 6/1972 | Damiano .............................. 71/78 |
| 3,744,988 | 7/1973 | Krumkalns et al. ................... 71/78 |
| 3,852,056 | 12/1974 | Draber et al. ......................... 71/78 |

*Primary Examiner*—Glennon H. Hollrah
*Attorney, Agent, or Firm*—Charles A. Huggett; Mitchell G. Condos; Howard M. Flournoy

[57] ABSTRACT

N-[3-(4-Methyl-3-cyclohexenyl)butyl]amines are novel compounds highly effective in plant growth regulation.

6 Claims, No Drawings

N-[3-(4-METHYL-3-CYCLOHEXENYL)BUTYL]AMINES AND THEIR USE AS PLANT GROWTH REGULATORS

CROSS REFERENCE TO RELATED APPLICATIONS

This is a Divisional of Ser. No. 221,384 filed Jan. 27, 1972, entitled N-[3-(4-methyl-3-Cyclohexenyl)Butyl]Amines, now U.S. Pat. No. 3,890,384.

BACKGROUND OF THE INVENTION

1. Field of the Invention

This invention relates to novel compounds, N-[3-(4-methyl-3-cyclohexenyl)butyl]amines. This invention also relates to methods and compositions of matter for controlling or selectively regulating growth of plants.

2. Prior Art

The growth of plants has long been regulated by employing manual or mechanical methods. For instance, gardeners and nursery men "pinch" or prune plants or trees by cutting the tip of the stems to redirect or stimulate the growth of new stems in preference to the growth of the main stem in order to produce fuller and bushier trees and plants with a generally lower profile. More recently this manual or mechanical step has been followed by a second step, the application of a chemical contact agent to control so-called suckers.

For example, in the case of tobacco plants, obtaining the maximum yield of tobacco of good quality requires removal of the flower or reproductive growth from the vegetative growth of the plant. This process is known as topping. If the topping is delayed beyond the early flower stage yields are significantly decreased with each day of the delay. Once the plant is topped by cutting, axillary growth between each leaf and stalk begins. This growth is termed sucker growth. Sucker growth must be controlled to prevent decreases in both yield and quality which are similar to those that result from not topping the tobacco plant. This is particulary important when mechanical harvesting is employed for the crop.

For many years suckers were individually pulled from the plants by hand several times during the growing season at a considerable labor cost. More recently a variety of chemical agents have been employed for this purpose with varying degrees of success. As one of the early contact treatments, the application by hand of mineral oil to the top of the stalk to run down and kill the sucker initials by contact was an improvement over the manual operation. But it was not completely satisfactory in providing only partial and short term control while introducing stalk and leaf rotting problems.

Subsequently, liquids containing maleic hydrazide derivatives like those described in Schoene et al. U.S. Pat. No. 2,805,926 were effectively sprayed as systemic agents for the control of suckers on much of the domestic tobacco crop. However these agents have their limitations, in that they should not be applied until tobacco flowers reach the late bloom stage in order to avoid retarding the growth of the leaves, and resulting in a loss in quantity of approximately 25 pounds less yield per acre for every day the topping of tobacco is delayed beyond the early flower stage. To minimize such losses, a number of dual treatments have been devised wherein a contact agent has been sprayed on the tobacco immediately after the topping in early bloom followed by treatment at an appropriate later date with a maleic hydrazide derivative for systemic action. The systemic agent acts within the plant system, and the timing of its application is critical because all parts of the plant are affected by it. On the other hand the contact agent affects only the exterior of the plant tending to inhibit new growth and to stimulate further growth of established leaves and thus produce larger and more desired leaves.

Among the known contact control agents are dimethyl dodecylamine acetate, esters of fatty acids, as exemplified by methyl caprates and mixtures of octanol and decanol dispersed in a suitable liquid carrier.

In contrast with the time consuming and higher labor costs of manual or mechanical topping, with the laborious topical application of a contact agent the compositions according to the present invention may be applied by spraying or other means of direct application as the sole mens of regulating plant growth.

Used for the control of suckers in plants such as tobacco are a series of long chain aliphatic ammonium salts which are disclosed and described in U.S. Pat. No. 3,223,517. Although these compounds are related to the instant compounds, they are nonetheless quite dissimilar in structure and in their growth regulating ability. The compounds according to the present invention are amines rather than ammonium salts and the long chain aliphatic radicals therein are unsaturated cyclic radicls rather than saturated straight chain aliphatic radicals as disclosed by the patent. Consequently such dissimilarity in chemical structure would not make the instant ompounds obvious for their intended use. Furthermore, the use of the patent does not disclose the ammonium salts to control both primary and secondary growth as do the instant amines. The elimination of mechanical topping by the use of compositions according to the present invention is a decided advantage and distinction over the ammonium salts of the patent and the prior art in general.

Thus a new series of compounds have now been found which when incorporated into suitable compositions overcomes to a large extent the prior art shortcomings described above.

SUMMARY OF THE INVENTION

The present invention relates to new compounds, to compositions of matter for controlling plant growth and to methods of treating plants with such compositions. These compositions of matter comprise at least one N-[3-(4-methyl-3-cyclohexenyl)butyl]amine and a carrier therefor. More specifically the invention relates to these compounds and their use as plant growth regulators. In particular, these compounds provide a method for the control of undesirable primary and secondary growth in such plants as tobacco, tomatoes, cotton, soybeans, etc.

In the case of tobacco, the application of the compounds according to the invention to intact tobacco plants (i.e., plants which have not been mechanically topped) destroys the terminal buds and the secondary buds. This effect is unknown for prior art conventional tobacco sucker control agents. The destruction of the terminal buds inhibits the apical dominance of the plant and destruction of the secondary buds inhibits sucker growth. In other words, application of the instant compounds to intact tobacco plants results in the same desireable effect as the now common two-step practice of mechanical topping, which inhibits apical dominance, followed by spraying of a chemical contact agent, which controls suckers. A single application may be sufficient; however, in some specific instances two applications of the compositions according to the invention may be required. Nevertheless, even though two applications may be required the disadvantages (1) of maintaining an inventory of different contact agents are eliminated; (2) the need for costly manual or mechanical topping of the plants is eliminated and the compositions provide a single agent which both controls suckers and destroys terminal buds. Furthermore, these compounds provide desirable plant growth effects and avoid injury to the desirable parts of the plant.

DESCRIPTION OF SPECIFIC EMBODIMENTS

The invention specifically deals with compounds having the general formula:

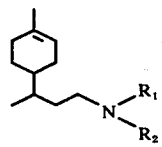

Wherein $R_1$ and $R_2$ are each selected from the group consisting of hydrogen, alkyl ($C_1$-$C_8$), alkenyl($C_2$-$C_8$), alkynyl ($C_2$-$C_8$), aralkyl($C_7$-$C_{14}$), heterocyclic alkyl, phenyl, heterocyclic aryl and combinations of these as parts of the same radical, which radical may have substituted thereon a member or members of the group consisting of halogen, nitro, hydroxy, alkoxy, phenoxy, substituted phenoxy, acetyl, cyano, alkylmercapto, mercapto, hydroxy, carbalkoxy, carboxy, carbamoyl, alkylamimo, dialkylamino, and combinations and multiples of these and wherein $R_1$ and $R_2$ may be joined by a linking agent X to form a heterocycle ($C_2$-$C_6$), which X may be selected from the group of common linkages consisting of oxy, carbonyl, carbonyloxy, aza, alkylaza, arylaza, diazo, hydrazo, thio, sulfinyl, sulfonyl, methano and substituted methano.

The invention also deals with a method for regulating plant growth by inhibiting terminal and secondary bud growth and controlling the axillary growth known as suckers comprising contacting said plant with an effective amount of a compound according to the invention.

Narrower aspects of the invention involve one or more of the above described compounds and/or compositions according to the invention. Especially preferred is N,N-dimethyl-N-[3-(4-methyl-3-cyclohexenyl)butyl]amine in a carrier material which includes a solvent or surfactant for dispersing the amine; the utilization of aqueous dispersions of said amines for treating the various plants and, an especially important embodiment, treatment of both topped and intact tobacco plants.

In general, the compound of this invention are prepared by mixing an equivalent amount of 3-(4-methyl-3-cyclohexenyl)butyraldehyde with an appropriate secondary amine and a catalytic amount of a hydrogenating catalyst in an appropriate solvent. The reaction mixture is shaken under pressurized hydrogen until an equivalent amount of hydrogen is consumed. The mixture is then filtered ad concentrated. Next the residue is distilled and pure N-[3-(4-methyl-3-cyclohexenyl)-butyl]amines recovered. Hereinafter the abbreviation [3 . . . butyl] will be used to represent [3-(4-methyl-3-cyclohexenyl)butyl]. The 3-(4-methyl-3-cyclohexenyl)butyraldehyde is a known compound and forms no part of this invention. Its preparation is described in U.S. Pat. No. 2,584,539 (1952) by R. B. Wearn and C. Bordencakand by W. A. Laxier in U.S. Pat. No. 2,584,539 (1952). Appropriate secondary amines are readily available from normal commercial sources. Non-limiting examples of hydrogenating catalysts are platinum, palladium, rhodium, platinum oxide, palladium oxide and nickel. Non-limiting examples of appropriate solvents are ethanol, methanol, benzene, ethyl ether, toluene, chloroform, and hexane. The pressure of hydrogen useful for this reaction may vary from 16 to 50 pounds per square inch.

Non-limiting examples of compounds embodied in this invention include:

N,N-dipropyl-N-[3 . . . butyl]amine; N,N-diisopropyl-N-[3 . . . butyl]amine; N-methyl-N-ethyl-N-[3 . . . butyl]amine; N-methyl-N-butyl-N-[3 . . . butyl]amine; N-methyl-N-allyl-N-[3 . . . butyl]amine; N-methyl-N-[3 . . . butyl]amine; N-propyl-N-[3 . . . butyl]amine; N-t-butyl-N-[3 . . . butyl]amine; N-cyclopropyl-N-methyl-N-[3 . . . butyl]amine; N-cyclohexenyl-N-[3 . . . butyl]amine; N-methyl-N-butenyl-N-[3 . . . butyl]amine; N-methyl-N-(2-morpholino)-N-[3 . . . butyl]amine; N-methyl-N-(3-piperidino)-N-[3 . . . butyl]amine; N-methyl-N-(3-piperazino)-N-[3 . . . butyl]amine; N-methyl-N-phenyl-N-[3 . . . butyl]amine; N-methyl-N-(p-chlorphenyl)-N-[3 . . . butyl]amine; N-methyl-N-benzyl-N-[3 . . . butyl]amine; N-methyl-N-(2-chloroethyl)-N-[3 . . . butyl]amine; N-methyl-N-(2-dimethylaminoethyl)-N-[3 . . . butyl]amine; N-mthyl-N-(2-methoxyethyl)-N-[3 . . . butyl]amine; N-methyl-N-(2-nitroethyl)-N-[3 . . . butyl]amine; N-methyl-N-(2-cyanoethyl)-N-(3 . . . butyl]amine; N-methyl-N-(2-carboxyethyl)-N-[3 . . . butyl]amine; N-83 . . . butyl]-1,3-oxazine; N-[3 . . . butyl]-2-methylpiperidine; N-[3 . . . butyl]-2,6-dimethylpiperdine; N-[3 . . . butyl]-3-methylpyrrolidine; and N-[3 . . . butyl]-1,2-oxazine.

The compositons according to the invention contain in addition to the novel amines conventional carrier materials. Many liquid carrier materials may be employed in combination with the N-[3 . . . butyl]amines including, inter alia, organic solvents of relatively low phytotoxicity, such as methanol, butanol, isopropanol, amyl acetate, acetic acid, methyl isobutylketone, xylenes, mineral oils, certain chlorinated hydrocarbons, (e.g. ethylene dichloride), butane, propane and other gasses compressed to the liquid state, as well as surfactants for dispersing the amines in water and water for such aqueous dispersions. As the surfactant component, anionic and nonionic emulsifiers or surface active agents are often preferred to cationic surfactants, however many of the latter type are also operative for dispersing the amines.

In general, almost any inert solid or liquid carrier material may be used as long as it is capable of dissolving or dispersing the amine to substantial dilution and which is not harmful to the plant for its intended use. Especially advantageous are materials that are commonly used as carriers for other treating compounds, for example, water, alcohol, ketones, amides, esters, mineral oils, vegetable oils, bentonite, diatomaceous earth, pyrophyllite, fullers earth, gypsum, cotton seed flour, and natural and synthetic clays.

In most instances, however, an aqueous carrier is preferred. Furthermore, the carriers may include binding agents for holding the amines in contact with the plant and/or various film-forming agents, as exemplified by mineral and ester waxes, and natural and synthetic resins and polymers, to minimize the loss of the amine from the treated plant by evaporation or the washing action of rain.

In carrying out the method of this invention for regulating plant growth, the treating agent may be applied to emerging plants in various ways. For instance, the compositions may be applied in a growth controlling amount in the form of solutions or aqueous dispersions, powders or by spraying.

In many instances, it may be preferable to apply the compositions as rather dilute solutions or dispersions of the amines over the top of the plant and around the upper portion of its foliage to the extent of run-off in order to insure contact with axils and terminal buds as the liquid drains down the stem of the plant. The plants are generally treated in an early stage of growth before the buds are well developed; however new shoots can also be treated.

The compositions and compounds of the present invention are excellent plant growth regulators, in that, they destroy both terminal buds and secondary buds, thereby, inhibiting apical dominance of the plant and sucker growth. Thus by the sole application of compositions according to the invention one achieves the same effect as mechanical topping and concomitantly controls sucker growth.

The quantities of the present compositions that are required for such purposes vary considerably as they are dependent upon a number of factors, including the size and type of plant undergoing treatment, the amines selected, the method of applying the agent, the state of plant growth and atmospheric conditions, such as temperature and rainfall. Accordingly, the quantity of active treating agent for any particular application is best determined by experiment. For example, in the case of young tobacco plants that have just been topped, sucker development often can be appreciably restricted by the application of about 0.1 to 1.0 ml of the agent in a suitably diluted liquid carrier per plant, but better results are usually obtained with a treatment involving at least two to three times as much of the amine; and these figures include the quantity of active material lost in the application by the run off of treating solution involved and thoroughly wetting all axils of each plant. If the plants are intact an appropriately greater amount of the amine composition will have to be used and a second treatment may in some cases be necessary.

For a better understanding of the nature, objects and advantages of this invention, reference should be made to the following detailed examples which are intended as illustrations rather than limitations on the scope on this invention.

EXAMPLE 1

N,N-Dimethyl-N-[3-(4-methyl-3-cyclohexenyl)butyl]amine

A 250 ml hydrogenation flask was charged with 50g (0.3 mole ) of 3-(4-methyl-3-cyclohexenyl)butyraldehyde, 15g (0.33 mole) of dimethylamine, 0.5 of platinum oxide and 80 ml of 95% ethanol. Cooling was required to control the initial exotherm. The reaction mixture was then shaken at ambient temperature under 20–40 lbs. of hydrogen until 0.3 mole of hydrogen was consumed. The mixture ws filtered and concentrated, and the residue was distilled yielding 38.4g of pure N,N-dimethyl-N-[3-(4-methyl-3-cyclohexenyl)butyl]amine: bp 95-101 (0.4mm); ir ($\tau$ max. film) 3.5 (s), 6.9 (s), 7.3 (s), 12.5 (m) micron; nmr (8 $CDCl_3$), 5.40 (m, 1H), 2.28 (s, 8H), 2.0 to 0.8 (m, 16H) ppm; ms (molecular ion) 195.

EXAMPLE 2

N-N-Diethyl-N-[3-(4-methyl-3-cyclohexenyl)butyl]amine

The procedure of Example 1 was followed using 50g (0.3 mole) of 3-(4-methyl-3-cyclohexenyl)butyraldehyde and 20g (0.33 mole) of diethylamine. Obtained following distillation was 38g of pure, N,N-deithyl-N-[3 ... butyl]amine as a clear, colorless liquid: bp 96°–99° (0.2mm); ir ($\delta$ max. film) 3.5 (s), 6.9 (s), 7.3 (s), 9.4 (m), 12.5 (m) microns, nmr ($\delta$ $CDCl_3$) 5.36 (m, 1H), 2.95 (m, 6H), 2.1 to 0.8 (m, 16H), 1.0 (t, 6H) ppm; ms (molecular ion) 223.

EXAMPLE 3

N-[3-(4-Methyl-3-cyclohexenyl)butyl]morpholine

The procedure of Example 1 was followed using 50g (0.3 mole) of 3- 4-methyl-3-cyclohexenyl)butyraldehyde and 29g (0.33 mole) of morpholine. Obtained following distillation was 51g of pure N-[3 ... butyl]morpholine as a clear, colorless liquid: bp 111–114° (0.15mm); ir ($\tau$ max. film) 3.5 (s), 6.9 (s), 7.9 (m), 8.9 (s), 12.5 (m) microns; nmr ($\delta$, $CDCl_3$) 5.35 (m, 1H), 3.68 (t, 4H), 2.36 (m, 6H), 2.1 to 0.8 (m, 16H) ppm; ms (molecular ion) 237.

EXAMPLE 4

N-[3-(4-Methyl-3-cyclohexenyl)butyl]pyrrolidine

The procedure of Example 1 was followed using 50g (0.3 mole) of 3-(4-methyl-3-cyclohexenyl)butyraldehyde and 24g (0.33 mole) of pyrrolidine. Obtained following distillation was 48.5g of pure N-[3 ... butyl]pyrrolidine as a clear, colorless liquid: bp 106°–108° (0.2mm) ir ($\tau$max. film 3.5 (s), 6.9 (s), 7.3 (s), 8.7 (s), 12.5 (m) microns; nmr ($\delta$, $CDCl_3$) 5.36 (m, 1H), 2.45 (m, 6H), 2.1 to 0.8 (m, 20H) ppm; ms (molecular ion) 221.

EXAMPLE 5

N-Methyl-N-[3-(4-methyl-3-cyclohexenyl)butyl]piperazine

The procedure of Example 1 was followed using 50g (0.3 mole) of 3-(4-methyl-3-cyclohexenyl)butyraldehyde and 33g (0.33 mole) of N-methyl-piperazine. Obtained following distillation was 55g of pure N-methyl-N-[3 ... butyl]piperazine as a clear, colorless liquid: bp 109°–110° (0.08mm); ir ($\tau$max. film) 3.6 (s), 6.9 (s), 7.8 (s), 8.6 (s), 9.8 (s), 12.5 (m) microns; nmr ($\delta$, $CDCl_3$)5.35 (m, 1H), 2.46 (broad s, 10H), 2.25 (s, 3H), 2.1 to 0.8 (m, 16H) ppm; ms (molecular ion) 250.

EXAMPLE 6

N-Methyl-N-(2-hydroxyethyl)-N-[3-(4-methyl-3-cyclohexenyl)-butyl]amine

The procedure of Example 1 was followed using 50g (0.3 mole) of 3-(4-methyl-3-cyclohexenyl)butyraldehyde and 25g (0.33 mole) of 2-methylaminoethanol. Obtained following distillation was 27g of pure N-methyl-N-(2-hydroxyethyl)-N-[3 ... butyl]amine as a clear, colorless liquid; bp 104°–106° (0.1mm); ir ($\tau$max. film) 3.0 (m), 3.5 (s), 6.9 (s), 9.6 (s), 12.5 (m) microns; nmr ($\delta CDCl_3$) 5.38 (m, 1H), 3.8 (broad m, 1H) 3.6 (m, 2H), 2.5 (m, 4H), 2.2 (s, 3H), 2.1 to 0.8 (m, 16H) ppm; ms (molecular ion) 225.

EXAMPLE 7

N-[3-(4-Methyl-3-cyclohexenyl)butyl]piperdine

The procedure of Example 1 was followed using 50g (0.3 mole) of 3-(4-methyl-3-cyclohexenyl)butyraldehyde and 28g (0.33 mole) of piperdine. Obtained following distillation was 31g of a mixture of N-[3 . . . butyl]piperdine and N-[3-(4-methylcyclohexyl)butyl]-piperdine; bp 89–91° (0.1mm); ir ($\tau$max. film) 3.5 (s), 3.7 (s), 6.9 (s), 7.3 (s), 8.7 (s), 9.0 (s), 9.7 (s), 11.6 (m), 12.6 (w) microns; nmr ($\delta$, CDCl$_3$) 5.37 (m, 1H), 2.95 to 2.55 (m, 6H), 2.0 to 0.8 (m, 22H) ppm; ms (molecular ion) 236 and 238.

Example 1 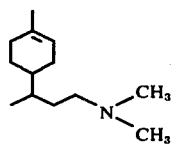

Example 2 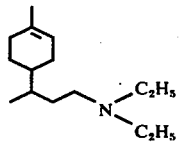

Example 3 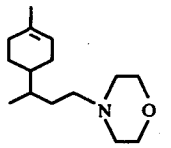

Example 4 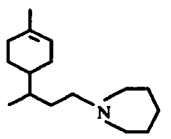

Example 5 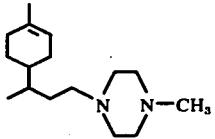

Example 6 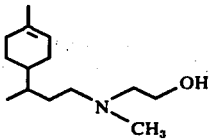

Example 7 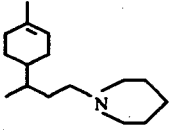

EXAMPLE 8

Tobacco Sucker Control Activity in Greenhouse Tests on Topped Tobacco

In greenhouse tests of individually potted tobacco plants which had been mechanically topped 1-2 days before treatment, aqueous dispersions of N-[3-(4-methyl-3-cyclohexenyl)butyl]amines (i.e., Examples 1–7) containing a commercial surfactant and a solvent were tested for sucker control under comparable conditions.

The surfactant serves the dual purpose of emulsifying or dispersing the aliphatic amines in water and also of improving the wetting characteristics of the final treating liquid on plants.

The dispersions were initially prepared in concentrated form by mixing 25 parts of Maran D potassium rosin soap paste with 25 parts of the N-[3-(4-methyl-3-cyclohexenyl)butyl]amine in 50 parts of methanol. The concentrated dispersions were diluted with water to provide a treating liquid with an aliphatic amine content of 3%, 2% and 1% by weight. An atomizer was employed to spray ten milliliters (ca. one ounce) of the diluting agent on the upper foliage of the topped tobacco plants.

The untreated tobacco plants were maintained as controls and were not subjected to any treatment.

Visual observations were made 22 days after treatment and weight of sucker growth was measured 5 weeks after treatment.

The results of these tests are set forth in Table I.

Table I

| COMPOUND | % CONC. | SUCKER CONTROL % WEIGHT INHIBITION[1] | PHYTO-TOXICITY[1] |
|---|---|---|---|
| Example 1 | 3 | 100 | Moderate |
| Example 1 | 2 | 100 | Trace |
| Example 1 | 1 | 100 | None |
| Untreated | — | 0 | None |

[1]Average of duplicate runs.

EXAMPLE 9

Tobacco Chemical Topping and Sucker Control Activity In Greenhouse Tests on Intact Tobacco The greenhouse tests in Example 9 were performed exactly as those in Example 8 except that the individually potted tobacco plants were not mechanically topped before treatment. The 1% aqueous dispersions of the aliphatic amines were prepared according to Example 8. An atomizer was employed to spray ten milliliters of the dilute agent on the top and upper foliage of the tobacco plants. Visual observations were made 22 days after treatment. The results of these tests are set forth in Table II.

Table II

| COMPOUND | % CONCENTRATION | OBSERVATIONS[1] |
|---|---|---|
| Example | 1 | All terminal buds killed or totally arrested. Apical dominance destroyed. Trace phytotoxicity to leaves and stems. Sucker growth initiated on upper axils. |
| Untreated, mechanically topped | | Apical dominance destroyed. Sucker growth initiated on upper axils. |

[1]Average of triplicate runs.

Although Examples 8 and 9 are drawn to tobacco plants it is to be understood that other plants such as tomatoes cotton, soybeans, and the like are within the scope of this invention.

Other disclosed compositions and/or compounds not exemplified in the above examples give equivalent, although not identical, results. Therefore, it will be apparent to those skilled in the art that the present compositions and/or compounds and treating methods are subject to many variations and modifications within the scope of the foregoing disclosure. Accordingly, this invention should not be construed as limited in any particulars except as it may be recited in the appended claims or required by the prior art.

What is claimed is:

1. A method for regulating growth of tobacco plants by inhibiting terminal and secondary bud growth and controlling the axillary growth known as suckers comprising contacting said plant with an amount effective to attain such regulation and control of a compound having the general formula:

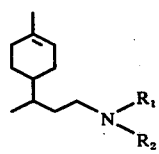

wherein $R_1$ and $R_2$ are each selected from the group consisting of hydrogen and alkyl ($C_1$-$C_8$).

2. The method according to claim 1 where the compound is N,N-di-methyl-N-[3-(4-methyl-3-cyclohexenyl-butyl]amine.

3. The method according to claim 26 where the compound is N,N-diethyl-N-[3-(4-methyl-3-cyclohexenyl-butyl]amine.

4. A composition for regulating the growth of tobacco plants comprising an effective amount of a compound as defined in claim 1 and an inert solid or liquid carrier.

5. The composition of claim 4 where the compound is N,N-dimethyl-N-[3-(4-methyl-3-cyclohexenyl)butyl]amine.

6. The composition of claim 4 where the compound is N,N-diethyl-N-[3-(4-methyl-3-cyclohexenyl)butyl]amine.

* * * * *

UNITED STATES PATENT AND TRADEMARK OFFICE
CERTIFICATE OF CORRECTION

PATENT NO. : 4,030,908
DATED : June 21, 1977
INVENTOR(S) : Jerry G. Strong

It is certified that error appears in the above-identified patent and that said Letters Patent are hereby corrected as shown below:

| | |
|---|---|
| Column 3, line 62 | "ad" should read --and--. |
| Column 4, line 33 | "N-83" should read --N-3--. |
| Column 8, Table II | Under COMPOUND, "Example" should read --Example 1--. |
| Column 10, Claim 3 | "26" should read --1--. |

Signed and Sealed this

Fourth Day of October 1977

[SEAL]

Attest:

RUTH C. MASON
*Attesting Officer*

LUTRELLE F. PARKER
*Acting Commissioner of Patents and Trademarks*